US008104338B2

(12) United States Patent
DiFoggio

(10) Patent No.: US 8,104,338 B2
(45) Date of Patent: *Jan. 31, 2012

(54) METHOD AND APPARATUS FOR ION-SELECTIVE DISCRIMINATION OF FLUIDS DOWNHOLE

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 725 days.

This patent is subject to a terminal disclaimer.

(21) Appl. No.: 12/118,368

(22) Filed: May 9, 2008

(65) Prior Publication Data

US 2008/0314139 A1 Dec. 25, 2008

Related U.S. Application Data

(63) Continuation-in-part of application No. 11/358,568, filed on Feb. 21, 2006, now Pat. No. 7,373,813.

(51) Int. Cl.
*E21B 47/08* (2006.01)
(52) U.S. Cl. .................................................. 73/152.55
(58) Field of Classification Search ............... 73/152.23, 73/152.54, 152.55

See application file for complete search history.

(56) References Cited

U.S. PATENT DOCUMENTS

| | | | |
|---|---|---|---|
| 3,890,502 A | 6/1975 | Dowling et al. | |
| 4,524,324 A | 6/1985 | Dickinson, III | |
| 4,698,500 A | 10/1987 | Scala | |
| 5,353,637 A | 10/1994 | Plumb et al. | |
| 6,346,813 B1 | 2/2002 | Kleinberg | |
| 6,995,899 B2 | 2/2006 | Aronstam | |
| 7,062,958 B2 | 6/2006 | Diakonov et al. | |
| 7,373,813 B2 * | 5/2008 | DiFoggio | 73/152.55 |
| 2002/0066309 A1 | 6/2002 | Tubel et al. | |
| 2003/0033866 A1 * | 2/2003 | Diakonov et al. | 73/152.55 |
| 2003/0134426 A1 | 7/2003 | Jiang | |
| 2003/0136673 A1 | 7/2003 | Pilloud | |
| 2003/0205083 A1 | 11/2003 | Tubel et al. | |
| 2003/0213691 A1 | 11/2003 | Peper | |
| 2004/0045350 A1 | 3/2004 | Jones et al. | |
| 2005/0092595 A1 | 5/2005 | Peterson | |
| 2005/0109098 A1 | 5/2005 | DiFoggio | |
| 2005/0133697 A1 | 6/2005 | Potyrailo | |
| 2005/0191428 A1 | 9/2005 | Buck | |

OTHER PUBLICATIONS

J. P. Janseens at al., Columbus: A Novel Sensor System for Domestic Washing Machines, Jun. 2002, pp. 1-9.

* cited by examiner

*Primary Examiner* — John Fitzgerald
(74) *Attorney, Agent, or Firm* — G. Michael Roebucki

(57) ABSTRACT

In a particular embodiment, a method and system are disclosed for measuring ion concentrations for a fluid and determining a degree of sample cleanup during sampling of a fluid downhole. The method includes but is not limited to deploying an ion selective sensor downhole, exposing the fluid to the ion selective sensor downhole, measuring ion concentrations of the fluid over time during sampling and estimating a degree of sample clean up from the ion concentration measurements. The system includes but is not limited to a tool deployed in a wellbore, an ion selective sensor in the tool, a processor in communication with the ion selective sensor and a memory for storing an output from the ion selective sensor.

20 Claims, 6 Drawing Sheets

METHOD AND APPARATUS FOR ION-SELECTIVE DISCRIMINATION OF FLUIDS DOWNHOLE

CROSS REFERENCE TO RELATED APPLICATIONS

This patent application claims priority from and is a continuation in part of U.S. patent application Ser. No. 11/358,568, now U.S. Pat. No. 7,373,813 filed on Feb. 21, 2006 entitled "A Method and Apparatus for Ion-selective Discrimination of Fluids Downhole by Rocco DiFoggio" which is incorporated herein by reference in its entirety.

FIELD OF THE DISCLOSURE

The present invention relates to the field of downhole fluid analysis and in particular to the determining a property of a fluid downhole.

BACKGROUND INFORMATION

In the oil and gas industry, formation testing tools have been used for monitoring formation pressures along a wellbore in a hydrocarbon bearing formation or reservoir, obtaining formation fluid samples from the wellbore and predicting performance of the reservoirs around the wellbore. Such formation testing tools typically contain an elongated body having an elastomeric packer that is sealingly urged against the zone of interest in the wellbore to collect formation fluid samples in storage chambers placed in the tool.

During drilling of a wellbore, a drilling fluid ("mud") is used to facilitate the drilling process and to maintain a pressure in the wellbore greater than the fluid pressure in the formations surrounding the wellbore. This is particularly important when drilling into formations where the pressure is abnormally high. If the fluid pressure in the borehole drops below the formation pressure, there is a risk of blowout of the well. As a result of this pressure difference, the drilling fluid penetrates into or invades the formations for varying radial depths (referred to generally as invaded zones) depending upon the types of formation and drilling fluid used. The formation testing tools retrieve formation fluids from the desired formations or zones of interest, test the retrieved fluids to ensure that the retrieved fluid is substantially free of mud filtrates, and collect such fluids in one or more chambers associated with the tool. The collected fluids are brought to the surface and analyzed to determine properties of such fluids and to determine the condition of the zones or formations from where such fluids have been collected.

One feature that most formation testing tools have in common is a fluid sampling probe. This may consist of a durable rubber pad that is mechanically pressed against the rock formation adjacent the borehole, the pad being pressed hard enough to form a hydraulic seal. Through the pad is extended one end of a metal tube that also makes contact with the formation. This tube ("probe") is connected to a sample chamber that, in turn, is connected to a pump that operates to lower the pressure at the attached probe. When the pressure in the probe is lowered below the pressure of the formation fluids, the formation fluids are drawn through the probe into the wellbore to flush the invaded fluids prior to sampling. In some formation tests, a fluid identification sensor determines when the fluid from the probe consists substantially of formation fluids; then a system of valves, tubes, sample chambers, and pumps makes it possible to recover one or more fluid samples that can be retrieved and analyzed when the sampling device is recovered from the borehole.

It is desirable that only uncontaminated fluids are collected, in the same condition in which they exist in the formations. Commonly, the retrieved fluids are found to be contaminated by drilling fluids. This may happen as a result of a poor seal between the sampling pad and the borehole wall, allowing borehole fluid to seep into the probe. The mud cake formed by the drilling fluids may allow some mud filtrate to continue to invade and seep around the pad. Even when there is an effective seal, borehole fluid (or some components of the borehole fluid) may "invade" the formation, particularly if it is a porous formation, and be drawn into the sampling probe along with connate formation fluids. The measurement made by the downhole instrument will be of a physical nature (i.e., electrical, acoustical, nuclear, thermal, dimensional, etc.) pertaining to some part of the wellbore environment or the wellbore itself. Other types of well data are collected at the surface; examples are core logs, drilling-time logs, mud sample logs, hydrocarbon well logs, etc. Still other logs show quantities calculated from other measurements; examples are movable oil plots, computed logs, etc.

SUMMARY OF THE INVENTION

In a particular embodiment, a method and system are disclosed for determining a degree of sample cleanup during sampling of a fluid downhole. The method includes but is not limited to deploying an ion selective sensor downhole, exposing the fluid to the ion selective sensor downhole, measuring ion concentrations of the fluid over time during sampling and estimating a degree of sample clean up from the ion concentration measurements. The system includes but is not limited to a tool deployed in a wellbore, an ion selective sensor in the tool, a processor in communication with the ion selective sensor and a memory for storing an output from the ion selective sensor.

A system and method for estimating a property of a fluid downhole are disclosed, including but not limited to a system for deploying an ion specific sensor at a first depth; exposing a first fluid to the ion specific sensor downhole; measuring an ion concentration for the first fluid and identifying the property from the ion concentration.

Examples of certain features of the invention have been summarized here rather broadly in order that the detailed description thereof that follows may be better understood and in order that the contributions they represent to the art may be appreciated. There are, of course, additional features of the invention that will be described hereinafter.

BRIEF DESCRIPTION OF THE FIGURES

For a detailed understanding of the present disclosure, references should be made to the following detailed description of the illustrative embodiment, taken in conjunction with the accompanying drawings, in which like elements have been given like numerals, wherein.

DETAILED DESCRIPTION OF AN ILLUSTRATIVE EMBODIMENT

Figure 1:
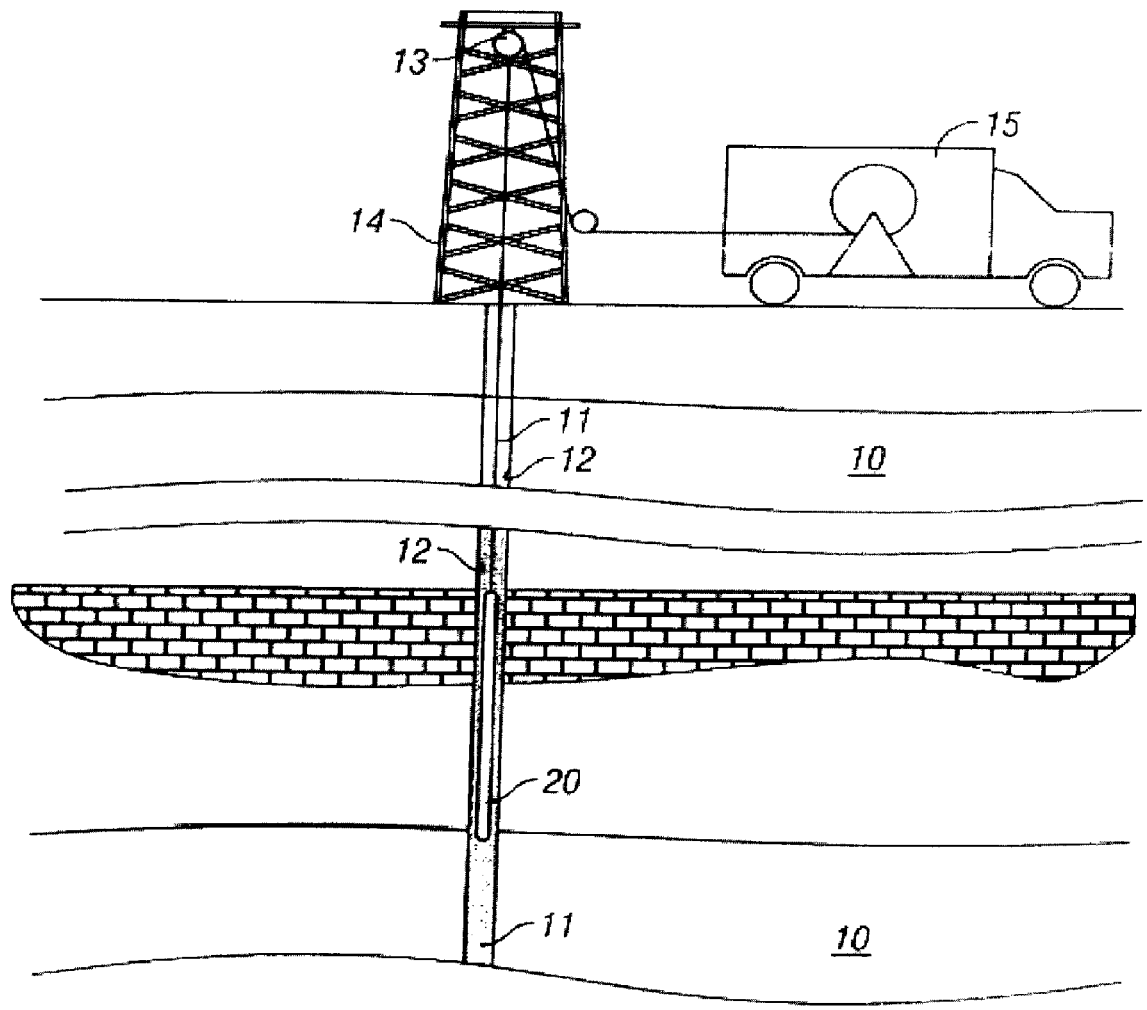
FIG. 1 is a schematic diagram of a sampling tool deployed in a bore hole in an illustrative embodiment.

In another illustrative embodiment, a method is disclosed for estimating a property of a fluid downhole, the method including but not limited to deploying an ion specific sensor at a first depth in a bore hole adjacent a formation; exposing a first fluid to the ion specific sensor downhole; measuring an ion concentration for the first fluid; and identifying the property of the fluid from the ion concentration. In another illustrative embodiment of the method the ion specific sensor further includes but is not limited to an ion specific field effect device. In another illustrative embodiment of the method, the method further includes but is not limited to monitoring decrease of a first fluid in the presence of a second fluid from the ion concentration during sample cleanup. In another illustrative embodiment of the method, the first fluid is a hydrocarbon selected from the group consisting of a gas, liquid and mixture of solids in a liquid.

In another illustrative embodiment of the method the ion specific sensor selects an ion from the set consisting of potassium, nitrogen and hydrogen. In another illustrative embodiment of the method, the method further includes but is not limited to identifying the property of the first fluid further includes but is not limited to locating a source for the fluid from the ion concentration measured for the first fluid. In another illustrative embodiment of the method, the method further includes but is not limited to measuring an ion concentration for a second fluid from a second layer downhole; and estimating a source for an undesirable fluid from the ion concentrations measured for the first fluid and the second fluid. In another illustrative embodiment of the method, the first fluid is from a first layer in a formation and the second fluid is from a second layer in the formation, the method further including but not limited to comparing the ion concentration for the first fluid to the ion concentration for the second fluid; and estimating compartmentalization for the formation from the comparing of the ion concentration for the first fluid to the ion concentration for the second fluid.

In another illustrative embodiment of the method, the ion selective sensor further includes but is not limited to a plurality of sensors each deployed at a different depth, the method further includes, is but not limited to estimating a source of a fluid having a particular ion concentration from a plurality of ion concentration measurements made by the plurality of sensors at different depths. In another illustrative embodiment of the method, the ion concentration further includes but is not limited to measuring a plurality of ion concentrations for the fluid at a single depth; and identifying a source of the fluid from the plurality of ion concentrations for the fluid. In another illustrative embodiment of the method, the method further includes but is not limited to measuring ion concentrations for fluids flowing from different layers in a formation. In another illustrative embodiment, a system for estimating a property of a fluid is disclosed, including but not limited to a wellbore; and a tool having an ion selective sensor deployed in a location within the wellbore, the tool further including but not limited to a processor in communication with the ion selective sensor; and a memory for storing an output from the ion selective sensor.

In another illustrative embodiment of the system, the tool further includes but is not limited to a plurality of tools forming an array of tools, each tool in the array having an ion selective sensor, the ion selective sensor further includes but is not limited to a plurality of ion selective sensors, wherein each of the plurality of ion selective sensors selects a different ion. In another illustrative embodiment of the system, the tool is deployed from one of the set consisting of a wireline, coiled tubing and a drill string. In another illustrative embodiment of the system the tool is a sampling tool. In another illustrative embodiment, an apparatus for estimating a source of a fluid in a wellbore, the apparatus including but not limited to a tool deployed in the wellbore, the tool having an ion selective sensor for measuring an ion concentration for a first fluid at a first depth in the borehole, the tool further including but not limited to a processor in communication with the ion selective sensor; a memory for storing an output from the ion selective sensor; and a computer program embedded in a computer readable medium containing instructions that when executed by the processor estimate the property of the undesirable fluid from the ion concentration.

In another illustrative embodiment of the apparatus, the computer program further includes instruction to estimate a property of a second fluid source downhole, instructions to measure an ion concentration for the second fluid from a second fluid flow from the second fluid source downhole. In another illustrative embodiment of the apparatus, the computer program further includes instructions to estimate a degree of sample clean up from a comparison of the ions concentrations over time during sampling. In another illustrative embodiment of the apparatus, the computer program further includes instructions to estimate a degree of compartmentalization from a comparison of the ions concentrations over time during sampling.

The term "pH" is a symbol used to designate the degree of acidity or alkalinity (basicity) of a water solution. The pH scale measures how acid or alkaline a solution is. The pH is directly related to the ratio of hydrogen ($H^+$) to hydroxyl ($OH^-$) ions present in the solution. The more hydrogen ions that are present, the more acidic the solution. If hydroxyl ions exceed hydrogen ions, the solution is basic, and if the two ions are present in equal amounts, the solution is neutral.

The pH scale ranges from 0 to 14, with the pH of pure water equaling 7.0. Values smaller than 7.0 indicate an increase in hydrogen ions (acidity); numbers larger than 7.0 indicate an increase in alkalinity. Because the scale is logarithmic, a pH of 6.0 represents 10 times more hydrogen ions than are present at pH 7.0, while a pH of 5.0 represents 10 times more hydrogen ions than are present at pH 6.0 and 100 times more hydrogen ions than are present at pH 7.0.

Thus, pH is an expression representing the negative logarithm of the effective hydrogen-ion concentration or hydrogen-ion activity (in gram equivalents per liter). The pH value is a unit of measure of the acid or alkaline condition of a substance. A neutral solution (as pure water) has a pH of 7; acid solutions are less than 7; basic, or alkaline solutions are above 7. The pH scale is a logarithmic scale; a substance with a pH of 4 is ten times as acidic as a substance with a pH of 5. Similarly, a substance with a pH of 9 is ten times more alkaline as a substance with a pH of 8.

Ion selective devices can discriminate between fluids (including gases or liquids) having different ion concentrations of a particular ion. Ion selective field effect transistors (Is-FETS) are devices that can be used to measure the concentration of particular ions, for example, ions including but not limited to Na, K or other ions. In an illustrative embodiment an ion selective device, for example, including but not limited to an IsFET, is provided. The IsFET is used along with a processor, memory and data base to measure and distinguish between ion concentrations of fluids in a formation adjacent a wellbore. Ion sensitive sensors enable distinction of one ion selective fluid from other fluids pumped from a formation by a sampling tool. The ion selective sensor, in an illustrative embodiment, an IsFET which enables measurement of ion concentrations in the fluids pumped from the formation. A processor, memory and data base are associated with the IsFET and housed in a tool for deployment into a borehole for sampling fluids from an adjacent formation.

The combination of the ion selective sensor, processor and memory distinguishes differences in particular ion concentrations of the fluids sampled from an adjacent formation through the wellbore wall. An array of IsFETS separated within a single sampling tool or an array of IsFETs separated within several separate sampling tools can be used to determine fluid concentrations by comparison or cross correlation of their responses of fluid sampled at different depths in the wellbore to sample fluids from different layers in the formation adjacent the wellbore. The different depths for sampling can correspond to different layers in the formation. For purposes of the present disclosure the terms "ion specific, ion selective and ion sensitive are used interchangeably to mean a device or sensor that has a preference for a particular ion. The terms ion selective sensor and ion selective device are also used interchangeably to mean a physical element that has a preference for a particular ion.

In another illustrative embodiment, a particular ion is selected for monitoring downhole, for example, K or Na. An ion selective sensor, for example, an IsFET device is lowered to different depths into a wellbore and ion concentration measurements made at each depth. In an alternative embodiment, an array of ion selective sensors, for example, an array of IsFET devices is placed into a sampling tool and deployed into a wellbore, each IsFET device in the array being deployed at a different depth. The depths of the single device or deployment depths of devices in the array can be selected to correspond with layer in the formation can be positioned. Perforations in the wellbore may correspond to different layers in the formation. In another particular embodiment each IsFET device in the array is incorporated into a sampling tool and attached to a wireline at a different depth.

A perforation locator, well known in the art, is also incorporated into the sampling tool help find perforations in the wellbore casing in a production well. Perforation location enables locating the ion selective sensor, the IsFET adjacent a formation layer for measurement to determine from which layer a particular fluid having a particular ion concentration is coming. A measurement is made for the ion concentrations at each depth associated with a formation layer. The measurements are made by an individual ion selective sensor or by an array of ion selective sensors, such as an array of IsFET devices.

An illustrative embodiment uses these ion concentration measurements to distinguish between fluids, such as between two or more waters (typically brines) or water and oil or other hydrocarbons based on ion concentration differences. In situations where unwanted water is produced, the ion concentration differences help to estimate which layer in a formation is producing most of the unwanted water so that a layer from which the unwanted fluid is coming can be avoided during production. Avoiding layers with unwanted fluids such as brine can save huge costs of producing brine and then having to dispose of unwanted brine.

Ion-specific field effect transistors can be used as ion selective devices to determine pH or other ion concentrations of fluids such as water in a production well. pH can be defined as=−10 Log 10 (Hydrogen Ion Concentration) and similarly pNa=−10 log 10 (Sodium Ion Concentration) and pK=−10 log 10 (Potassium Ion Concentration). The IsFET devices can be used to measure ion concentrations to distinguish between one formation brine from another formation brine to distinguish formation waters that have come from different zones (layers) in the formation.

In a particular embodiment, pH can be measured with an ion selective field effect transducer form MESA+Research Institute of the University of Twente and a commercially available thick film miniaturized silver/silver chloride reference electrode. A linear temperature correction can be used for the ISFET/reference electrode system.

Figure 2:
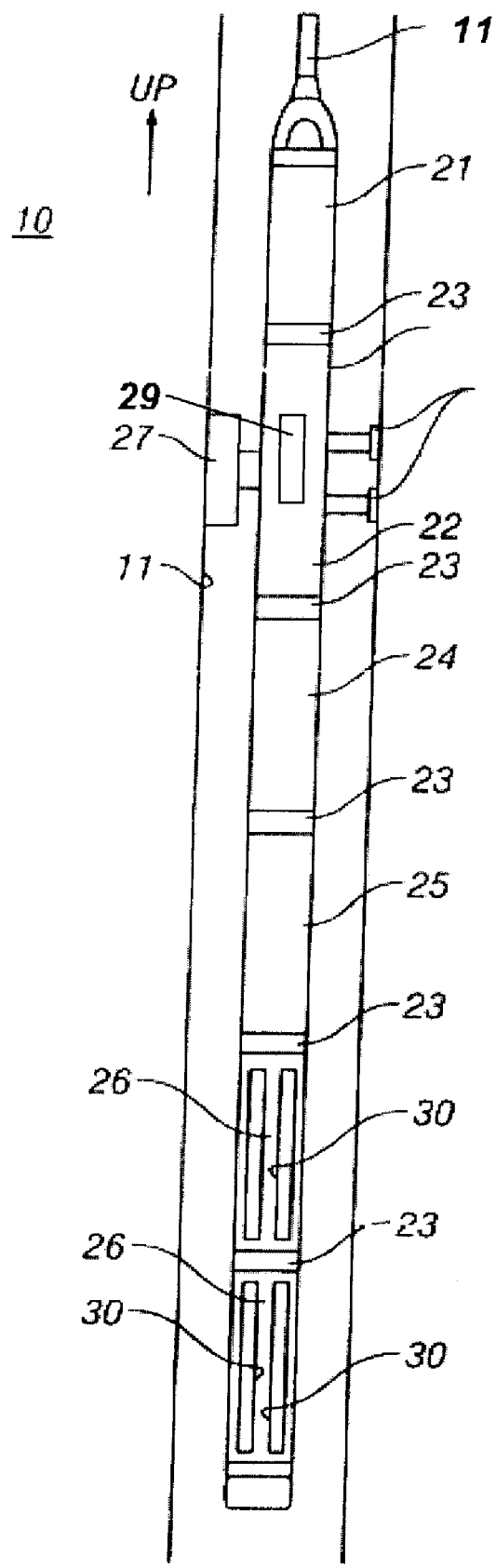
FIG. 2 is a schematic diagram of a sampling tool in another illustrative embodiment.

Turning now to FIG. 1, FIG. 1 schematically represents a cross-section of earth 10 along the length of a wellbore penetration 12. Usually, the wellbore will be at least partially filled with a mixture of liquids including water, drilling fluid, and formation fluids that are indigenous to the earth formations penetrated by the wellbore. Suspended within the wellbore 12 at the bottom end of a wireline 11 is a formation fluid sampling tool 20. The wireline 11 is often carried over a pulley 13 supported by a derrick 14. Wireline deployment and retrieval is performed by a powered winch carried by a service truck 15, for example. Pursuant to a particular illustrative embodiment, a sampling tool 20 is schematically illustrated by FIG. 2. The formation fluid extractor 22 comprises an extensible suction probe 27 that is opposed by bore wall feet 28. Both, the suction probe 27 and the opposing feet 28 are hydraulically extensible to firmly engage the wellbore walls.

Construction and operational details of the fluid extraction tool 22 are well known in the art. Such sampling tools comprise an assembly of several tool segments that are joined end-to-end by the threaded sleeves or mutual compression unions 23. An assembly of tool segments appropriate for the present invention may include a hydraulic power unit 21 and a formation fluid extractor 23. Below the extractor 23, a large displacement volume motor/pump unit 24 is provided for line purging. Below the large volume pump is a similar motor/pump unit 25 having a smaller displacement volume that is quantitatively monitored. One or more electronics and sensor sections 29 are incorporated into the tool. The electronics and sensor section is described more fully with respect to FIG. 5. Below the large volume pump is a similar motor/pump unit 25 having a smaller displacement volume that is quantitatively monitored. Ordinarily, one or more sample tank magazine sections 26 are assembled below the small volume pump. Each magazine section 26 may have three or more fluid sample tanks 30.

Figure 3:
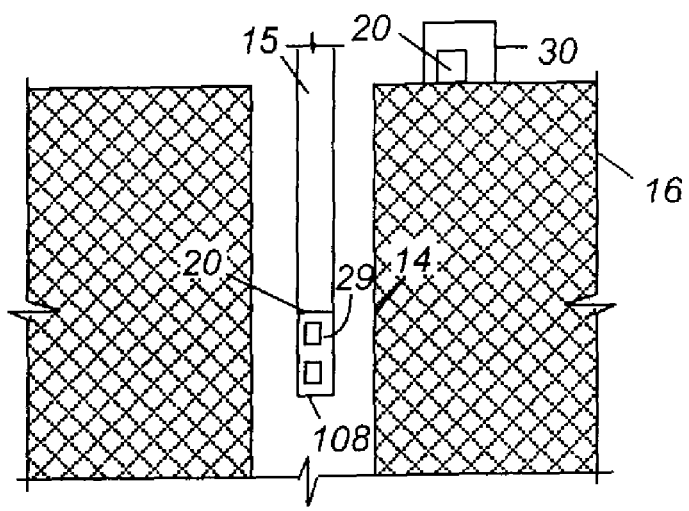
FIG. 3 is a schematic diagram of another illustrative embodiment deployed from a drill string in a wellbore.
Figure 4:
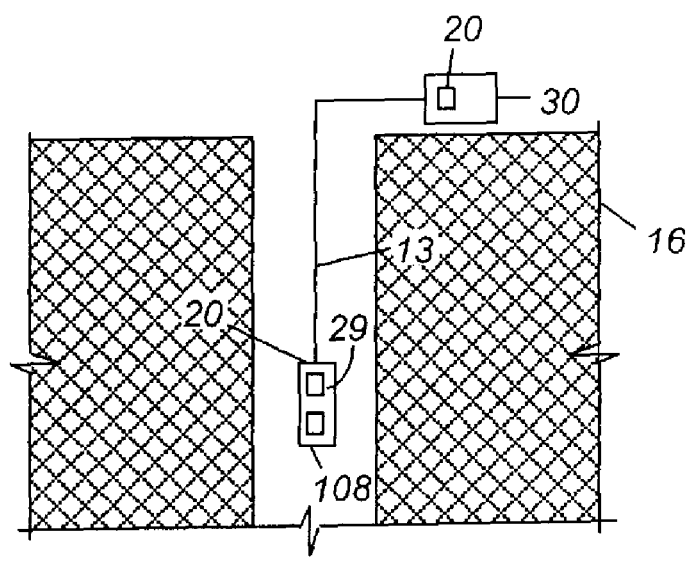
FIG. 4 is a schematic diagram of another illustrative embodiment deployed from a coiled tubing in a wellbore.

In another embodiment, the IsFET device or ion-sensitive sensor is deployed from a drill string in an open well or during monitoring while drilling. FIG. 3 depicts an illustrative embodiment deployed from a drill string in a wellbore. In another embodiment, the IsFET device or ion-sensitive sensor is deployed from coiled tubing in an open well or during monitoring while drilling. FIG. 4 depicts an illustrative embodiment deployed from coiled tubing in a wellbore.

Figure 5:
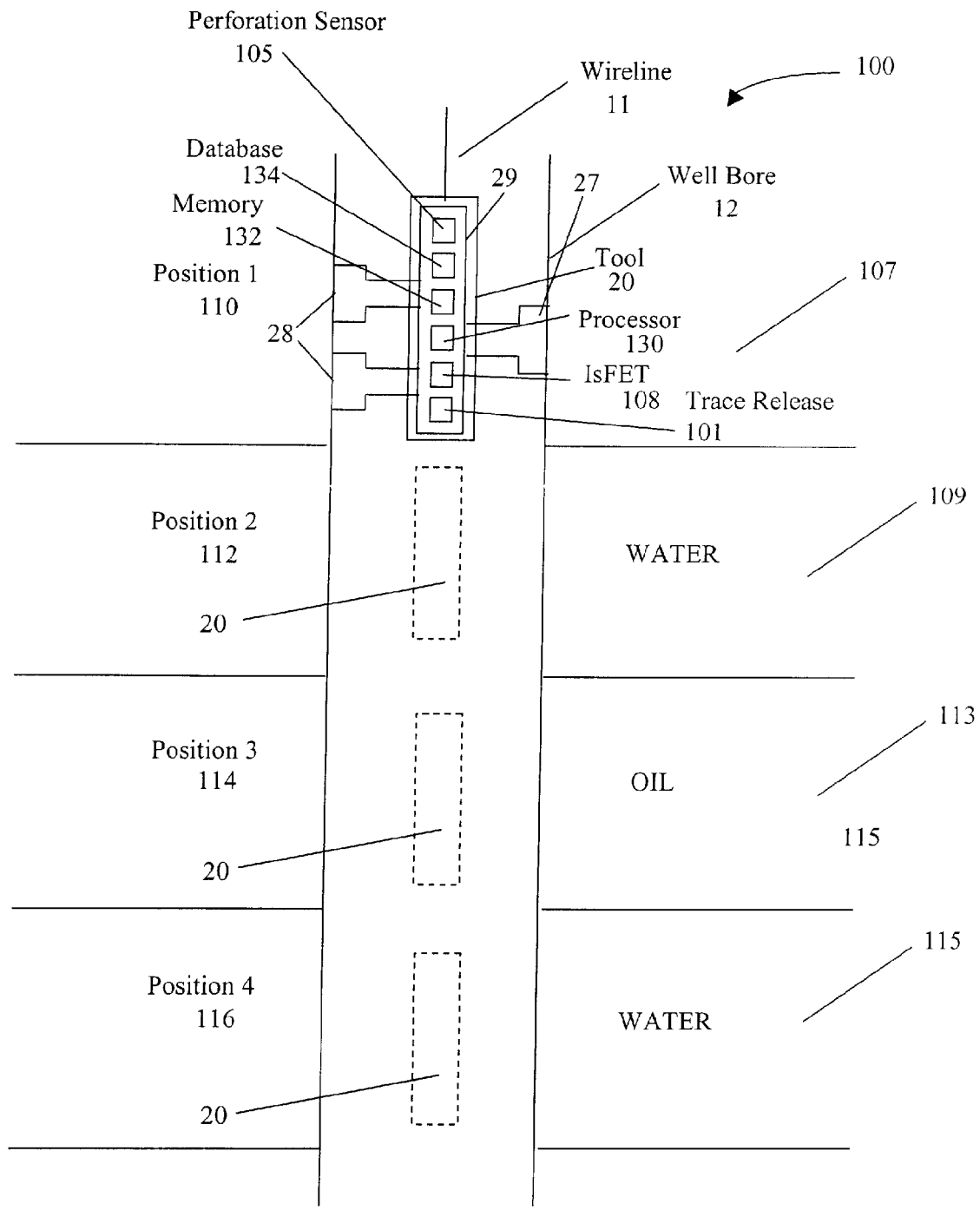
FIG. 5 is a schematic diagram of an illustrative embodiment of a tool containing an ion-sensitive sensor deployed downhole from a wireline at different depths in a production well.

Turning now to FIG. 5 an illustrative embodiment is shown deployed in a wellbore. As shown in FIG. 5, an illustrative embodiment 100 is depicted deployed in a wellbore 102. A tool 20 is deployed in a wellbore 102 from wireline 103. The tool 20 contains a processor 106 and an ion sensitive device, such as an ion sensitive field effect transistor (IsFET) 108, memory 132, database 134 and perforation locator 105. A tracer release unit 101 is provided in the tool for release of a fluid having an ion concentration detectable by the ion sensitive sensor 108 is contained in the tool 20. In a particular embodiment, the IsFET device is small approximately 1 mm$^2$ surface area on a side. Thus an array of IsFETs can be easily located in a single tool. The small IsFET devices are also low mass and thus resistant to vibration.

The wellbore 102 penetrates a formation consisting of different layers 109, 113 and 115. These layers may each have a different characteristic that affects the ion concentration that may vary over time. For example, during a particular time period all three formation layers 109, 113 and 115 may produce oil. After a period of time and after significant production, layers 109 and 115 may produce water or brine and layer 113 produce predominantly oil. The tool 20 can be positioned adjacent each formation layer 109, 113 and 115 to determine the ion concentration for fluids flowing from the formation layer adjacent the perforation.

Tool 20 contains ion sensitive device 108, processor 130 and memory 106. The processor takes digital samples of ion sensitive sensor data from the ion sensitive sensors in the ion sensitive device and stores the samples in processor memory. Processor memory may further include a data base in memory. The memory may include an embedded computer readable medium containing instructions that when executed by the processor perform the method and functions described herein.

When the tool 20 is in position 1 110, the ion sensitive sensor 108 senses the ion concentration, that is a count for a particular ion per unit volume, for example, brine, water and oil from all first layer in the formation 108. In the position 110 the tool housing the ion sensitive field effect transistor 108 can sense the ion concentrations of the fluids sampled from the first layer 107 of the formation adjacent wellbore 12. The processor 106 is utilized to control the ion sensitive field effect transistor (IsFET) 108 and to process and compare measurements of ion concentrations for fluids sampled by tool 20 and sensed by the IsFET 108.

In an illustrative example scenario, at position 110 the processor analyzes measurements from the ion sensitive sensor 108 in the tool and determines an ion concentration of the fluid sampled from first layer 107. In a production environment, a well operator wants to find the source of or the perforation in the wellbore casing leading to the layer that is the source of the excess hydrogen ion brine and seal off that perforation. In a preproduction environment, the well operator may forego perforating the borehole wall adjacent a formation layer or seal an existing perforation adjacent the layer that, based on the ion concentration measured by the tool 20 and IsFET 108, is likely to or is actually producing more brine than oil. This is preferable to disposing of an unwanted formation fluid, such as acidic brine after the unwanted fluid has been brought to the surface.

Samples of fluid are taken from formation layers 107, 109, 113 and 115 respectively. In position 2 112 the ion sensitive device 108 in tool 20 samples and measures the ion concentrations for fluids from formation layer 109. In position 3 114 the ion sensitive device 108 in tool 20 measures ion concentrations for fluids sampled from formation layer 115. In position 4 116 the ion sensitive device 108 in tool 20 samples and measures ion concentrations for fluids from formation layer 115.

In an illustrative embodiment the tool in position 1 samples fluid from an adjacent formation layer, such as a particular acidic brine with a particular ion concentration and thus seeks to determine which layer from which an increased flow of water having a hydrogen concentration originates. Lowering the tool to position 2 the ion sensitive device, in an illustrative embodiment an IsFET senses the ion concentration associated with fluid sampled from formation layer 109. In position 3, 114 the ion sensitive device 108 in tool 20 senses fluid sampled from formation layer 113. In position 4 116 the ion sensitive device 108 in tool 20 senses the flow 131 from formation layer 115.

Once the source layer of the undesirable excess hydrogen ion brine or fluid flow having high hydrogen ion concentration is identified it can associated with one of the layers in the formation. The layer from which the undesirable flow is coming, can then be sealed off or avoided by not perforating the wellbore adjacent that layer, to prevent or substantially reduce the flow of hydrogen ion brine or fluid from that layer. During or after drilling of the wellbore, historical samples from the formation layers adjacent the wellbore can be stored and later used to identify which layer in the formation is contributing to a production of an undesirable fluid. The historical samples can be compared to determine a degree of compartmentalization or connectivity between formation layers. During production, sealing off of a layer the perforation reduces the amount of water in the fluid produced from the formation.

In another illustrative embodiment, the ion selective sensor can be used during sampling of formation fluids to monitor sample cleanup to determine when a sample from the formation is substantially cleaned up, that is, substantially consisting of formation fluid after having pumped fluid from the formation initially containing drilling fluid mixed in with formation fluid. The drilling fluid invades the formation and mixes with formation fluid during sampling. After pumping fluid from the wellbore for a few minutes or hours, the drilling fluid is removed during sample pumping and the remaining fluids pumped during sample are substantially formation fluid with the drilling fluid removed.

In an illustrative embodiment the hydrocarbons, brines or salty water from each of the formation layers can be identified by their ion concentration and thus differentiated as to their source from one of the three layers. In an illustrative embodiment the formation layers adjacent the wellbore are separated by 30-50 feet. Over this distance of 30-50 feet between layers the brines or hydrocarbons are likely to have different ion compositions. Brines, however, might have roughly the same resistivity, thus a resistivity measurement of the brines would not differentiate between them. The small composition of difference between the brines coming from each layer helps to identify from which layer increased water production fluid is coming. Perforation locations can be sensed by numerous methods well known in the art such as a pin wheel spinning more rapidly nearer a perforation indicating an increased flow.

In another embodiment, the ion concentrations for formation fluids are sensed for each depth, perforation and/or formation layer during monitoring while drilling or during wireline operations in an open well before production and logged in an ion concentration log for future reference. Thus, when a particular ion concentration appears in excess in a production well, the ion concentration log can be referenced to determine which perforation associated with a particular layer is the source of the excess ion concentration. The perforation contributing to the excess ion concentration can then be sealed.

In another particular embodiment a sampling tool including an ion sensitive sensor is used in an open hole to take samples of different zones or layers in the formation thereby determining their ion concentrations for reference later in production to be associated with ion concentration measurements from ion sensitive devices, such as IsFETS. These ion concentration measurements help to determine the location of formation layer perforation that needs to be filled due to an increased flow of undesirable fluid, such as brine from that particular layer. The measurements can also be taken during monitoring while drilling logs in which a sampling tool could sample the brine zones or the ion concentrations associated with particular layers in the formation.

Figure 6:
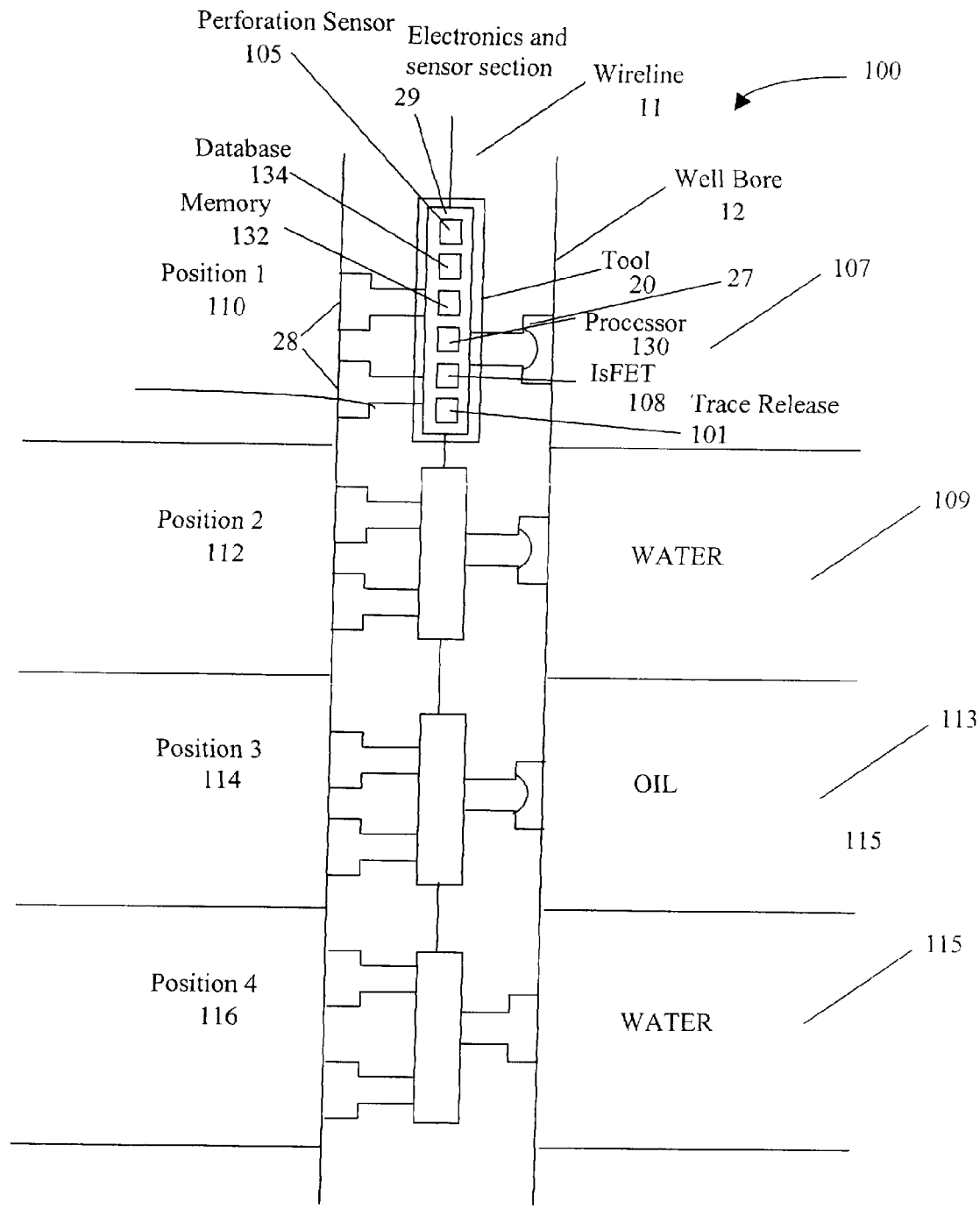
FIG. 6 is a schematic diagram of an illustrative embodiment of an array of ion-sensitive sensors deployed downhole from a wireline in a wellbore.

Turning now to FIG. 6, in another particular illustrative embodiment, an array of tools having 200 ion selective sensors, in the illustrative example, IsFETs 111, 113, 115 and 117, is deployed in the production well. The ion concentration measurements between the ion sensitive devices 111, 113, 115 and 117 in the array can be compared and cross correlated to determine ion. A particular ion concentration can be tracked between tools.

Figure 7:
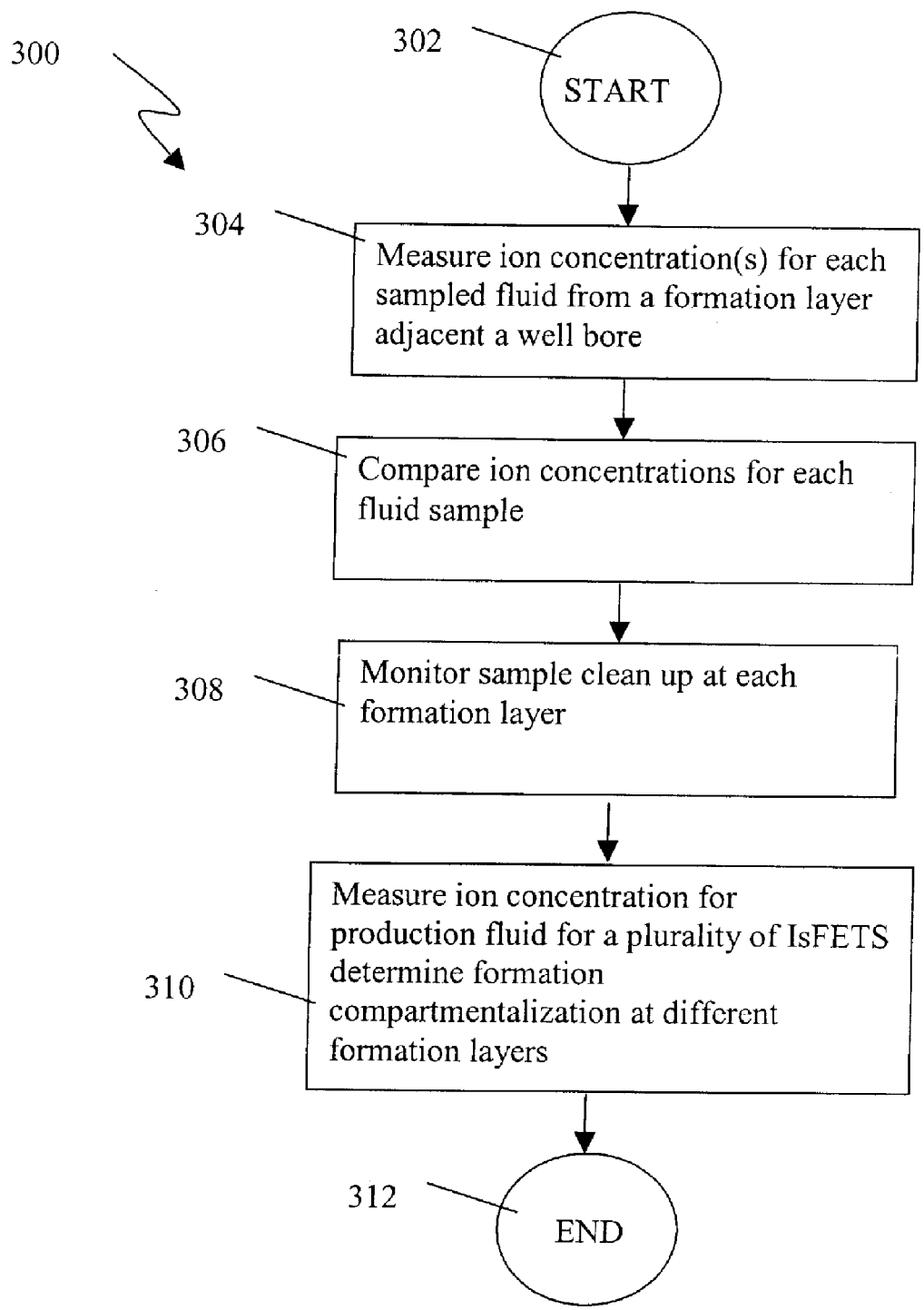
FIG. 7 is a flow chart for functions performed in an illustrative embodiment.

Turning now to FIG. 7 a flow chart of a method in an illustrative embodiment is provided. As shown in FIG. 7 an illustrative embodiment 300 is depicted in measuring ion concentrations during sample cleanup starting at different levels in a formation adjacent a wellbore. The depth or location for each formation layer is determined, an ion concentration is measured near each layer by ion sensitive sensor 108 and a data sample of the measurement is taken by processor 106. The data sample is stored in a memory 132. Each measurement is measured over time to determined when a particular formation sample is cleaned up, that is, when the sample represents a steady state percentage of formation fluid having drilling fluid substantially removed from the sample. In another embodiment, an array of ion selective sensors, for example IsFETs is provided in each tool. Each IsFET is selected to sense a different ion. Thus, a multiplicity of ion sensitive measurements for a multiplicity of ions can be made in a single tool at each depth. In another embodiment, several tools are deployed, each having at least one IsFET so that multiple samples at different depths in the formation can be obtained one at a time or concurrently.

While the foregoing disclosure is directed to the exemplary embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated.

The invention claimed is:

1. A method for identifying a fluid downhole, the method comprising:
    deploying an ion specific sensor at a first depth in a bore hole adjacent a formation;
    exposing a first fluid to the ion specific sensor downhole at a first depth;
    measuring an ion concentration for the first fluid at the first depth;
    deploying the ion specific sensor at a second depth in a bore hole adjacent a formation;
    exposing a first fluid to the ion specific sensor downhole at a second depth;
    measuring an ion concentration for the first fluid at the second depth; and
    identifying a location of a source for the first fluid from the ion concentrations at the first depth and the second depth.

2. The method of claim 1, wherein the ion specific sensor further comprises an ion specific field effect device.

3. The method of claim 1, further comprising:
    monitoring a decrease of the first fluid in the presence of a second fluid from the ion concentrations.

4. The method of claim 3, wherein the first fluid is a hydrocarbon selected from the group consisting of a gas, liquid and mixture of solids in a liquid.

5. The method of claim 1, wherein the ion specific sensor selects an ion from the set consisting of potassium, nitrogen and hydrogen.

6. The method of claim 1, the method further comprising:
    measuring an ion concentration for a second fluid from a second depth downhole, wherein the first fluid is from a first layer in a formation and the second fluid is from a second layer in the formation, the method further comprising:
    comparing the ion concentration for the first fluid at the first depth to the ion concentration for the second fluid at the first depth;
    comparing the ion concentration for the second fluid to the ion concentration for the second fluid at the second depth;
    and
    estimating compartmentalization for the formation from the comparing of the ion concentrations at the first and second depth for the first fluid to the ion concentrations at the first and second depth for the second fluid.

7. The method of claim 1, wherein the ion selective sensor further comprises a plurality of sensors each deployed at a different depth, the method further comprising:
    estimating a source of the first fluid having a particular ion concentration and a second fluid having a particular ion concentration from a plurality of ion concentration measurements made by the plurality of sensors at different depths.

8. The method of claim 1, wherein measuring the ion concentration further comprises:
    measuring a plurality of ion concentrations for the first fluid at the first depth; and
    identifying a source of the first fluid from the plurality of ion concentrations for the first fluid.

9. The method of claim 1, further comprising:
    measuring ion concentrations for a plurality of fluids flowing from different layers in a formation.

10. The method of claim 1, wherein identifying the first fluid further comprises:
    estimating connectivity for the formation from the ion concentration measurements at the first depth and the second depth.

11. The method of claim 10, further comprising:
    measuring an ion concentration for a second fluid at the first depth and at the second depth downhole; and
    estimating a source for the second fluid from the ion concentrations measured for the first fluid at the first depth and the second depth and the second fluid at the first depth and the second depth.

12. A system for identifying a fluid comprising:
    a wellbore; and
    a tool having an ion selective sensor in fluid communication with the fluid in a location within the wellbore, the tool further comprising a processor in data communication with the ion selective sensor;
    a memory embedded in a non-transitory computer readable medium for storing an output from the ion selective sensor at a first depth in the formation; and
    a computer program embedded in the non-transitory computer readable medium containing instructions that when executed by the processor identify a depth for a source of the fluid from the output of the ion selective sensor.

13. The system of claim 12, wherein the tool further comprises a plurality of tools forming an array of tools, each tool in the array having an ion selective sensor.

14. The system of claim 12, wherein the ion selective sensor further comprises a plurality of ion selective sensors, wherein each of the plurality of ion selective sensors selects a different ion.

15. The system of claim 12, wherein the tool is deployed from at least one of a wireline, coiled tubing and a drill string.

16. The system of claim 15, wherein the tool is a sampling tool.

17. An apparatus for identifying a fluid at a particular depth in a wellbore, the apparatus comprising:
- a tool deployed at a first depth in the wellbore, the tool having an ion selective sensor for measuring an ion concentration for a first fluid at a first depth in the borehole, the tool further comprising a processor in communication with the ion selective sensor;
- a memory embedded in a non-transitory computer readable medium for storing an output from the ion selective sensor; and
- a computer program embedded in the non-transitory computer readable medium containing instructions that when executed by the processor identify a source of the fluid at the first depth from the ion selective sensor output.

18. The apparatus of claim 17, the computer program further comprising:
- instructions to measure an ion concentration for the second fluid from a second fluid at the first depth; and instructions to identify the second fluid downhole from the ion concentration for the second fluid.

19. The apparatus of claim 18, the computer program further comprising:
- instructions to estimate a degree of change in ion concentrations from a comparison of the ions concentrations over time during sampling.

20. The apparatus of claim 18, the computer program further comprising:
- instructions to estimate a degree of compartmentalization from a comparison of the ions concentrations.

\* \* \* \* \*